(12) United States Patent
Robert

(10) Patent No.: US 8,535,212 B2
(45) Date of Patent: Sep. 17, 2013

(54) CENTRIFUGAL BLOOD PUMPS WITH REVERSE FLOW WASHOUT

(75) Inventor: Jarvik Robert, New York, NY (US)

(73) Assignee: Robert Jarvik, New York, NY (US)

( * ) Notice: Subject to any disclaimer, the term of this patent is extended or adjusted under 35 U.S.C. 154(b) by 0 days.

(21) Appl. No.: 13/076,079

(22) Filed: Mar. 30, 2011

(65) Prior Publication Data

US 2012/0253103 A1    Oct. 4, 2012

(51) Int. Cl.
*A61M 1/10*    (2006.01)

(52) U.S. Cl.
USPC .......................................................... 600/16

(58) Field of Classification Search
USPC .......................................................... 600/16
See application file for complete search history.

(56) References Cited

U.S. PATENT DOCUMENTS

| | | | | | |
|---|---|---|---|---|---|
| 1,771,939 | A | * | 7/1930 | Rees | 415/204 |
| 2,694,492 | A | * | 11/1954 | Rumpf et al. | 209/714 |
| 4,008,010 | A | * | 2/1977 | Fauconnet | 417/405 |
| 5,772,394 | A | * | 6/1998 | Yokota et al. | 415/56.1 |
| 5,824,070 | A | * | 10/1998 | Jarvik | 623/3.13 |
| 6,030,188 | A | | 2/2000 | Nojiri et al. | |
| 6,866,625 | B1 | | 3/2005 | Ayre et al. | |
| 7,476,077 | B2 | | 1/2009 | Woodard et al. | |
| 7,762,941 | B2 | * | 7/2010 | Jarvik | 600/16 |
| 2003/0144574 | A1 | | 7/2003 | Heilman et al. | |
| 2006/0013707 | A1 | | 1/2006 | Oklejas et al. | |
| 2009/0069854 | A1 | | 3/2009 | Keidar et al. | |

FOREIGN PATENT DOCUMENTS

CN    101718281 A    6/2010

OTHER PUBLICATIONS

Maurice L. Adams, "Rotating Machinery Vibration: From Analysis to Troubleshooting, Second Edition", Dec. 23, 2009, p. 254.*
Peerless Pump / LaBour Taber "LaBour TFA Pump", Brochure LB-011, Copyright 2005.*
International Search Report for PCT/US12/31205.

* cited by examiner

*Primary Examiner* — Carl H Layno
*Assistant Examiner* — Erin Piateski
(74) *Attorney, Agent, or Firm* — Troutman Sanders, LLP

(57) ABSTRACT

Blood pumps used as heart assist devices are commonly powered by an external battery and control system. If the external power is interrupted, such as by damaging an external cable, patients will have backflow across the pump. If the flow is too high, they may decompensate and die. If the backflow is relatively low, patients can survive until power is restored, but their blood pump must be sufficiently washed to prevent thrombus. Centrifugal blood pumps have been designed for good pumping performance, low blood damage, and avoidance of thrombus when they are running. The present invention recognizes the need to also provide enough washing to prevent thrombus when the pump power is turned off. The invention provides centrifugal pumps with triple or quadruple volute designs, or with axial flow impellers on the same shaft as the centrifugal pump impeller to help drive the rotor in reverse and enhance washing even with relatively low backflow. Also, in the preferred embodiment the centrifugal rotor is supported by low friction mechanical blood immersed bearings, to avoid contact of the rotor with the housing that creates small poorly washed crevices where thrombus can form.

14 Claims, 5 Drawing Sheets

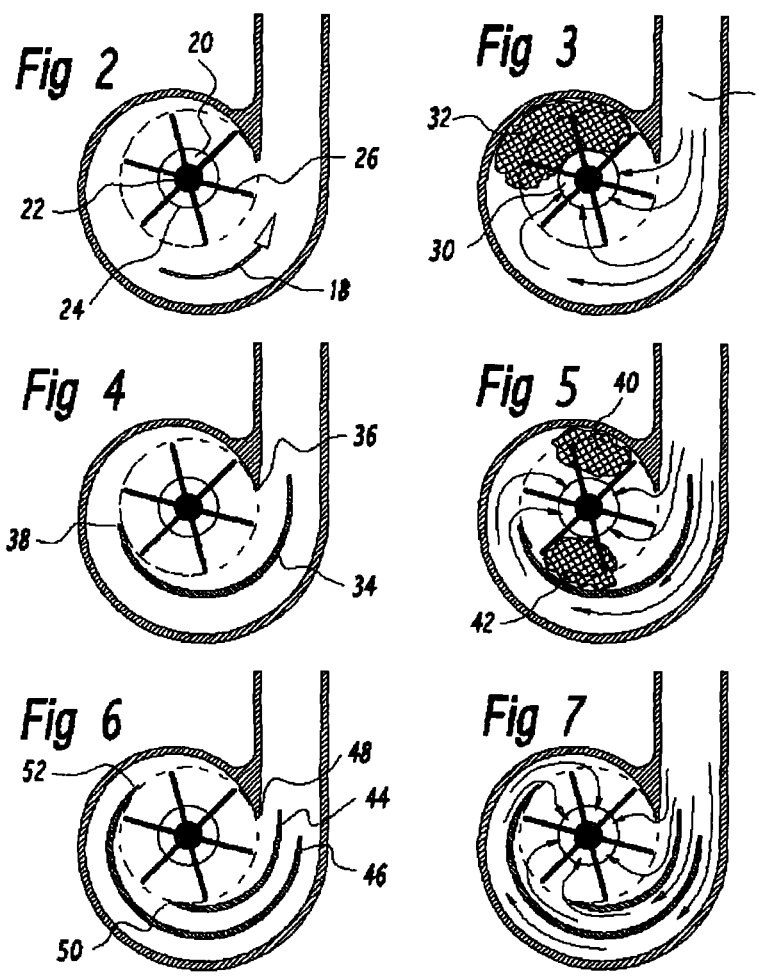

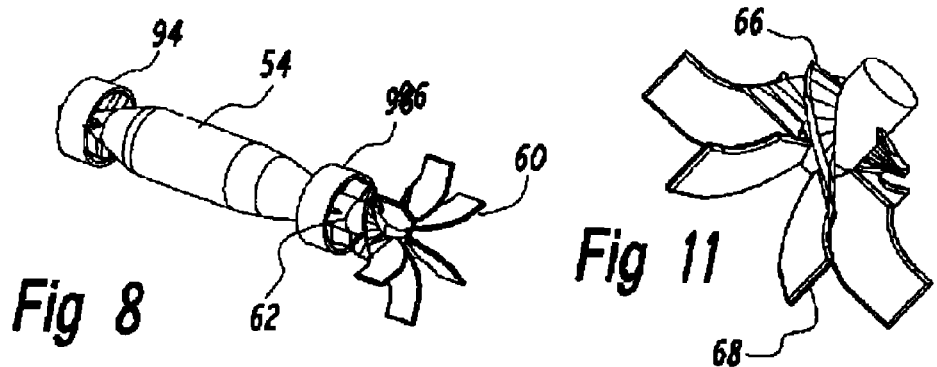
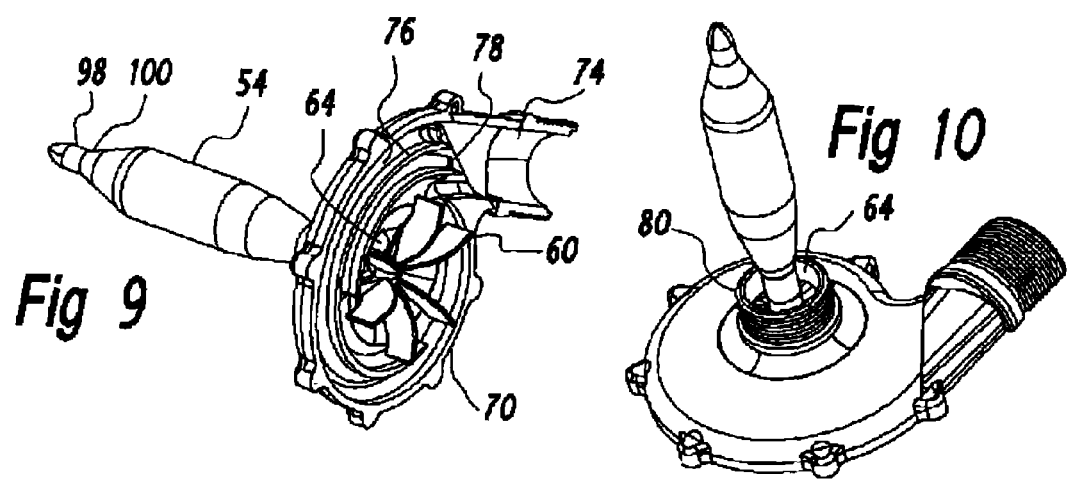

CENTRIFUGAL BLOOD PUMPS WITH REVERSE FLOW WASHOUT

BACKGROUND

Mechanical circulatory support has become widely applied in recent years. The number of patients treated with rotary blood pumps now exceeds the number of patients treated with heart transplant. Hydrodynamic rotary blood pumps include axial flow, mixed flow, centrifugal flow, and hybrid configurations. The mechanical principles of operation of these pumps have been developed, and their design and structure has largely been determined, by the need to meet the hemodynamic requirements of heart failure patients while avoiding excessive blood damage, and avoiding thrombus formation or bleeding resulting in the need for anticoagulation.

The Jarvik 2000 is an axial flow ventricular assist device that has sustained patients for more than seven years. We have experience with more than 300 patient years of support. We have learned that patient safety is enhanced if the patient has enough residual pumping function of their natural heart to maintain life long enough to switch to backup external equipment if the pump stops due to accidental damage to the external control system, batteries, or cables. When patients are supported for many years their external heart assist system components are exposed to all sorts of accidents that should be viewed as inevitable. For example, a Jarvik 2000 patient was carrying his control system and batteries in a camera bag worn on a shoulder strap. His mechanical heart within his chest was powered by a cable that had a connector attached where the wires exit the skin. When the patient was out shopping, a purse snatcher grabbed the camera bag off his shoulder and ran away with it. The cable pulled free of the connector and the pump then stopped because it lost power. Fortunately, the control system has a loud alarm that sounds if the pump stops. This frightened the purse snatcher, who threw the camera bag on the ground and ran away. Because the Jarvik 2000 has low regurgitant flow when turned off, the patient retained consciousness and was able to walk about a block to the place where the bag was left, and reconnect his artificial heart. If any rotary blood pump has high regurgitant flow, this will overwhelm the ability of the patient's natural heart to maintain sufficient forward flow pumped, and the patient will collapse and may die if the pump is not restarted immediately.

The prior art and the literature has numerous examples of pumps designed to avoid blood damage, and to avoid thrombus, by the use of sufficiently high flow washing, and the avoidance of excessive shear, which can damage the blood. There is very little prior art dealing with rotary blood pumps adapted to be safe when turned off.

The present invention provides blood pumps that are safe when turned off because they have low regurgitant flow and because the specific pump structure washes out all of the blood contacting surfaces to prevent stagnant regions susceptible to the formation of blood clots.

Left Ventricular Assist devices (LVADs) usually receive their blood inflow from the left ventricular apex, although other connections are sometimes used. The pump provides its outflow to a vascular graft sutured to the aorta. If the pump stops the pressure in the aorta is high enough to cause backflow through the aortic graft and into the left ventricle. This is functionally the same as high regurgitation of the aortic valve. The patient's weakened natural heart will fail rapidly if the backflow is too much. Generally, patients tolerate the reverse flow through the Jarvik 2000, which is less than 1 L/min., and remain conscious and able to function, sometimes for hours.

But other clinically applied axial flow LVADs, including the HeartMate II, the MicroMed DeBakey VAD, the Berlin Heart Incor, all have regurgitant flow of over 2 L/min. when turned off. Clinically applied centrifugal pumps including the HeartWare HVAD, the Ventracor, and the Terumo Duraheart also have high regurgitant flow, in excess of 2 L/min. None of these pumps is safe when turned off even briefly in most patients, who quickly go into heart failure and may die.

For all hydrodynamic blood pumps the volume of regurgitant flow is determined by the differential blood pressure across the device and the resistance of the blood flow channels within the pump, attachment cannulae, and grafts. Limitation of regurgitation may be accomplished by the use a flow channel restriction having a relatively small cross sectional area. But for patient safety it is not enough to limit the regurgitant flow to a value below 1 L/min. The pump must also be designed with sufficient washing of all blood contact surfaces under the low flow conditions to prevent thrombus formation.

Centrifugal pumps are especially subject to thrombus formation, because the blood inlet is in the central position, near the axis of rotation of the impeller, and the outlet is tangential located at the largest diameter of the pump chamber in which the impeller rotates. Thus, when stopped, the backflow takes the path of least resistance from the tangential outflow tube to the central inlet opening. Therefore, washout flow of the side of the pump chamber opposite the outlet is relatively poor and stagnant blood is subject to clotting. In centrifugal pump designs using magnetic suspension, hydrodynamic suspension, or partial magnetic with partial hydrodynamic suspension, the pump rotor will crash against the inner walls of the pumping chamber (pump casing) if power is lost, and come to rest in contact with the pump casing. There is so much friction that the rotor cannot be rotated by fluid forces, and the narrow gap regions between the rotor and casing will be especially susceptible to clotting.

This is unfortunate, because centrifugal blood pump designs have some particular advantages compared to axial flow pumps used for VADs. The centrifugal design permits wider gaps between the impeller and casing with lower shear and subsequently lower blood damage. Although red blood cells can withstand high shear for the very brief times occurring in the gaps of axial blood pumps, other types of blood damage, such as fracture of the von Willebrands factor molecule, are thought to be related to shear. Centrifugal blood pumps also have higher efficiency than axials, which is advantageous to increase battery life.

The present invention provides centrifugal blood pumps that are safe to stop, because the rotors are mounted on mechanical bearings and remain free to spin when stopped, and because a unique triple volute or quadruple volute structure is used to provide high washout to all portions of the impeller when the pump is turned off. A screw type inducer or axial flow impeller may be combined with a centrifugal or mixed flow impeller to facilitate back driving of the rotor when power is off. The rotor would then acts like a turbine and may be spun in reverse by the backflow of blood driven by the pressure gradient between the aorta and the pump inlet.

Most centrifugal pumps use a single volute design that results in unbalanced lateral forces on the impeller bearings, due to the non-radial symmetry of the fluid forces. This results from the non-symmetrical geometry of the pump volute. Use of a double volute design, having a splitter blade balances the radial fluid forces and results in more uniform balanced radial forces on the pump bearings. Some centrifugal blood pumps utilize the double volute design to balance the bearing forces. This improves the washout of the impeller when the pump is stopped, but is not optimal. Better washout is obtained by using a triple volute design with two splitter blades, or as many as three or four splitter blades. If too many splitter blades are used, the flow channels become excessively restricted, cause excessive resistance, and may themselves become loci of thrombus. Depending on pump size, triple or quadruple volute designs are optimal.

OBJECTS OF THE INVENTION

1. It is an objective of the present invention to provide centrifugal and mixed flow blood pumps that are safe if turned off for at least three minutes.

2. It is a further object of the present invention to provide centrifugal and mixed flow blood pumps that do not form thrombus within any of their flow channels when turned off for at least three minutes, with usual anticoagulation.

3. Another objective is to provide centrifugal and mixed flow blood pumps that have rotors that are spun by the blood pressure gradient across the pumps when they are not powered, so that washing of all blood contacting surfaces is enhanced compared to pump rotors that don't spin when off.

4. An additional object of the invention is to provide centrifugal or mixed flow blood pumps that are both safe to turn off and are designed to cause minimal damage to the blood, including damage to blood cells, platelets, and breakage of large molecules into smaller fragments.

5. It is a still further objective of the present invention is to provide high reliability centrifugal and mixed flow blood pumps in which the impellers do not contact the pump housing when the power is turned off.

6. It is an objective of the present invention to distribute the backflow through the pump relatively uniformly across each of the blades of the impeller when the pump is not powered.

7. It is an object of the invention to employ triple or quadruple volute designs, having two or three splitter blades, in centrifugal or mixed flow blood pumps, to improve blood flow washing when the pumps are not powered.

8. It is also an object of the invention too provide centrifugal of mixed flow blood pumps having a restricted flow path cross sectional area and high enough resistance to prevent excessive flow regurgitation sufficient to cause sudden cardiac decompensation, loss of consciousness, and death, if the pump suddenly loses power.

THE FIGURES

FIG. 2 is a cross sectional illustration of a single volute centrifugal pump (similar to the prior art) showing the direction of rotation of the impeller when the pump is turned on.

FIG. 3 is a cross sectional illustration of the same pump as FIG. 2 showing the pattern of reverse flow when the pump is turned off and not rotating. The area of reduced or stagnant blood flow susceptible to thrombus formation is shown by the cross hatched area.

FIG. 4 is a cross sectional illustration of a double volute centrifugal pump (similar to the prior art) having one splitter blade.

FIG. 5 is an illustration of the pump shown in FIG. 4 when the pump is stopped and the rotor is stationary. The reverse flow pattern is illustrated by the arrows, and two areas of reduced or stagnant blood flow susceptible to thrombus formation are shown by the cross hatching.

FIG. 6 is a cross sectional illustration of a triple volute centrifugal pump of the present invention having two splitter blades.

FIG. 7 is an illustration of the same pump shown in FIG. 6 showing the reverse flow pattern when the pump is turned off indicated by the arrows. A similar flow pattern, washing the spaces between all of the impeller blades also occurs when the pump is turned off and the impeller is rotating in the reverse direction.

FIG. 8 is a three dimensional illustration of the pump impeller of FIGS. 2-7, also showing the rotor shaft and mechanical bearings upon which the shaft is supported for rotation within the blood-stream.

FIG. 9 is a three dimensional illustration of the pump impeller and shaft in position relative to one half of a split pump casing, which is formed as a spiral volute flow chamber and the two splitter blades that divide the flow to create the triple volute structure.

FIG. 10 is a three dimensional illustration showing the central inflow orifice of the casing, with the rotor and impeller axis of rotation normal to the plane of the inflow opening.

FIG. 11 is a three dimensional illustration of the impeller of the preferred embodiment of the invention, having three blades each beginning at the upstream portion with an axial flow pump like generally helical portion and blending into a radial blade portion characteristic of a radial flow centrifugal pump.

SPECIFIC DESCRIPTION OF THE INVENTION

Figure 1A:
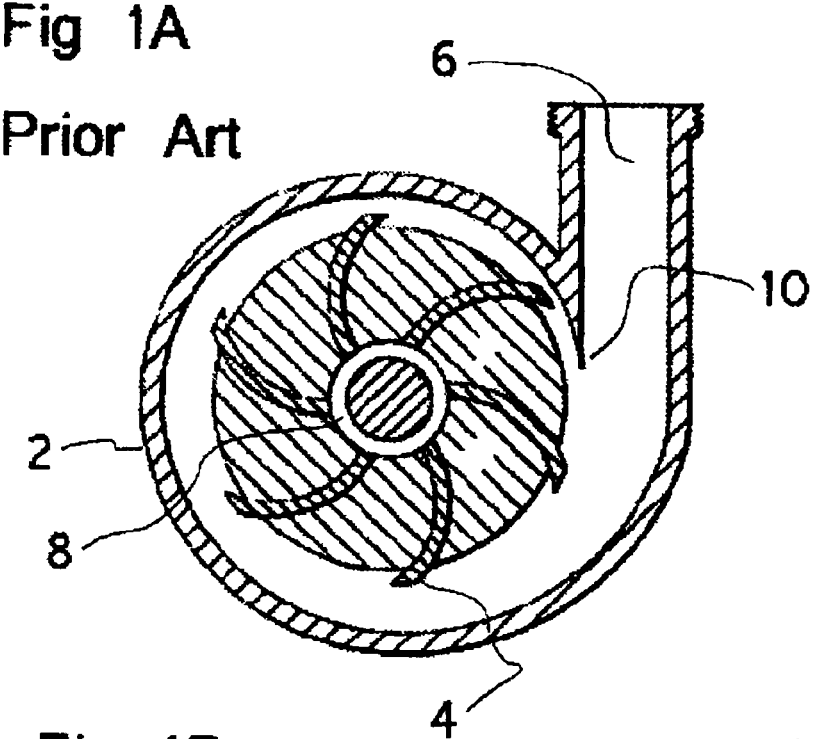
FIG. 1A is an illustration of a typical centrifugal flow blood pump with a single volute (prior art).
Figure 1B:
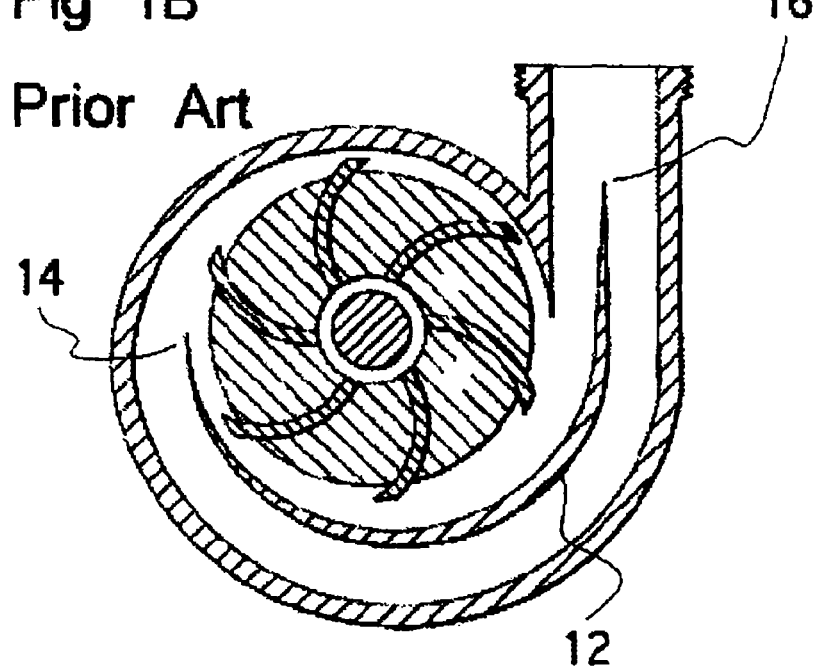
FIG. 1B is an illustration of a centrifugal flow blood pump with a dual volute (prior art).

FIG. 1A shows the basic prior art structure of a centrifugal pump having a spiral casing 2, with an impeller 4, and volute that is comprised of the spiraling casing and tangential outflow tube 6. The flow enters centrally through an inflow opening 8, and exits tangentially through the outflow tube 6. As seen in FIG. 1A the impeller rotates counterclockwise, and it is seen that the fluid forced to the periphery of the casing by the action of the impeller proceeds along a channel of gradually enlarging cross-sectional area from the position known as the cutwater 10, to the outflow tube. In the prior art double volute centrifugal pump structure shown in FIG. 1B, a partition known as a splitter blade 12, divides the spiraling flow channel into two portions, each occupying approximately 180°. In the double volute design there are two cutwater structures, 14, 16, such that two flow channels are formed that join at the outflow tube.

In the single volute design flow proceeds uniformly as shown by the arrow 18 in FIG. 2. Blood enters centrally via the opening 20 between the hub of the impeller 22 and the opening in the center of the casing 24. The impeller illustrated has six impeller blades, one of them indicated at 26. When the impeller is rotated at its normal design speed, all portions of the casing and outflow tube are well washed by flowing blood. It is a widely known principle that stagnant blood is prone to clotting, whereas blood moving at high enough velocity (above about 1 m/sec) will not clot if the flow channels are made of a polished blood compatible material such as titanium alloy. If the outflow pressure is high, and the impeller speed is too low, backflow may occur even with the pump running. In U.S. Pat. No. 5,368,554 Blood Pumping System with Selective Backflow Warning, Nazarian et. al. utilize a flow meter and specific electronics detectors to accurately activate an alarm if backflow occurs. If backflow occurs while the pump is running, reasonable washing of all of the pump casing and impeller surfaces is expected. But if the impeller stops, the flow will take the path of least resistance from the outflow 28, to the inflow 30, as shown by the arrows in FIG. 3, and a substantial portion of the pump indicated by the cross hatch 32, will experience poor washing and will be subject to clotting. If the pump uses a magnetically or hydrodynamically suspended rotor, and the power to operate the pump is interrupted, the rotor will lose suspension, and will "crash" against the casing, either immobilized there by magnetic forces, or by gravity and friction. A very small crevice especially prone to thrombus may exist, which makes these types of pumps unsafe to stop. Use of low friction blood immersed bearings in the present invention, FIGS. 12-94, 98, 96, and 102, prevents the rotor from crashing against the housing, and allows the rotor to be turned in reverse by fluid flowing along the impeller blades.

The present invention recognizes that if the pump driving power is lost, backflow will occur, and uses the triple or quadruple volute structure to augment the washing of all impeller and casing surfaces.

FIG. 4 shows a double volute structure, as from the prior art, with only one splitter blade 34, and two cutwater structures, 36, 38. FIG. 5 shows the same pump with the impeller stopped, showing the backflow around the splitter and through the volutes, indicated by the arrows. The washing is improved compared to the single volute design in FIG. 3, but there are two poorly washed areas, shown by the cross hatched lines at 40 and 42. A careful search of the prior art has revealed that the reason for using the double volute design has always been to balance the radial load on the impeller bearings, which is well known in the centrifugal pump art. But no reference is found to designing a double volute blood pump to improve the washing of all impeller and casing surfaces if the pump is stopped. And no triple volute blood pumps at all have been revealed by our search. The triple volute structure is superior to the double volute for washing the surfaces if the rotor is stopped. FIG. 6 shows the two splitter blades of our preferred embodiment, 44, 46 that create three cutwater structures, 48, 50, 52. Referring to FIG. 7, the arrows show that reverse flow, from the outflow tube back into the pump casing, is divided into three streams by the splitter blades, and washes the spaces between all impeller blades. There is no area of stasis such as occurs in the single and double volute designs. Thus the comparison of single and double volute washout when the impellers are stopped is shown to present a significant risk of thrombus formation in part of the casings and around part of the impellers. By contrast, the triple volute design achieves better washing of all impeller and casing surfaces.

Besides the use of the triple or quadruple volute designs, washout of any centrifugal pump when the driving power is turned off is improved if the rotor spins in reverse, driven by the differential pressure between the outflow (arterial pressure) and the inflow, (intraventricular pressure). To be safe when the power is off, the backflow must not be too high, or else the patient will rapidly go into severe heart failure and will die. Thus, the unpowered pump rotor should spin in reverse with low flow, not to exceed a mean reverse flow of 0.75 L/min. This requires the pump rotor to be suspended on low friction mechanical bearings. Use of an axial flow type impeller mounted on the rotor upstream of the centrifugal impeller helps the blood flow and pressure to spin the rotor, because the axial flow type impeller, having a generally helical shape, works as a turbine when exposed to reverse flow. FIG. 8 shows the pump rotor and impeller supported on mechanical blood immersed bearings, of the type disclosed in my U.S. Pat. No. 7,762,941, Blood Pump Bearings with Separated Contact Surfaces. The rotor 54, contains the motor magnet within it, and is held at each end by wear resistant stationary bearing support rings with support blades 94, 96 that support rotating bearing components on the rotor, best seen as 98, and 102 in FIG. 12.

The impeller, 60, is fixed to the rotor at 62 after its hub and shaft portion are passed through the central inlet hole in the casing 64, best seen in FIG. 10.

FIG. 11 shows a six blade impeller of the preferred embodiment. Three of the six blades have a generally helical portion at the inflow side of the impeller 66, that smoothly joins with a radial portion of the blade 68. The three other blades attach to the impeller hub such that blades with a generally helical axial flow part alternate with blades of principally radial design. Many other impeller types could be used in pumps of the present invention, including impellers with separated axial flow blades (sometimes called an inducer). Mixed flow impellers combined with triple volute casings can also be used.

FIG. 9 shows the rotor 54, with the casing 70, having its inlet opening 64, and outlet tube 74. One of the splitter blades in the casing is indicated at 76, and the other splitter blade is shown at 78. As seen in FIG. 10, the helical portion of the impeller is located within a generally axial tube like member 80, that acts as the inlet of the pump casing.

Figure 12:
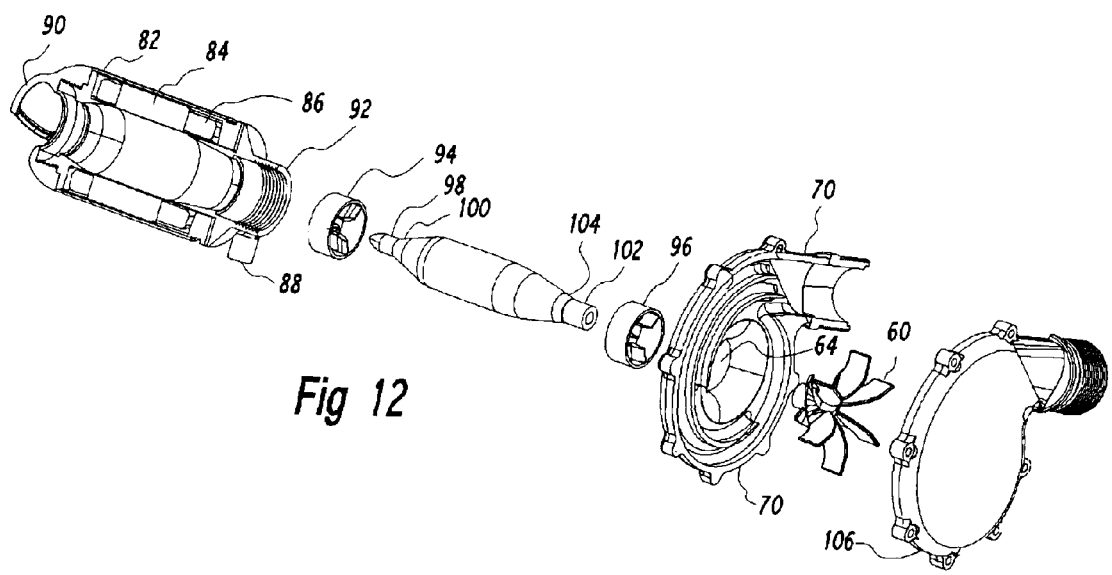
FIG. 12 is an exploded view of a blood pump of the present invention, having a longitudinally sectioned motor housing, seen on the left, the rotor and bearings, the impeller, and the two split halves of the triple volute casing.

Referring to FIG. 12 a pump motor housing 82, encloses a motor stator usually including laminations 84, and windings 86. Power cables enter the housing through a conduit 88, and connect to an electrical power source (not shown). On the inflow side of the motor housing, a cage, 90, may be included if the motor is to be implanted within the heart. The cage prevents myocardial tissue from obstructing the inflow. A threaded connector portion of the motor housing 92, is designed to attach the centrifugal pump casing 70, to the motor housing via the threaded casing inlet tube, 80. The inflow side bearing ring with inward blades 94, and outflow side bearing ring 96, also with inward blades, support the inflow side rotating ceramic bearing that has a cylindrical portion 98, and a tapered portion, 100. The outflow side bearing ring has inward projecting blades that support the rotating bearing component. This includes a cylindrical portion 102 and a tapered portion 104. The structure of both the inflow side and outflow side bearings includes mating cylindrical and conical tapered surfaces that are orientated to bear thrust loads applied towards either end of the rotor, thus confining the rotor and permitting free rotation with very little axial motion. The impeller is rigidly affixed to the rotor and the relative axial positions of the various pump parts are designed such that the rotor is located centrally between the inflow side of the casing 70, and the other side of the casing 106. The surfaces of these two parts, and the surfaces of the splitter blades are manufactured to be precisely flat where they contact one another when assembled. The casing halves are thus able to be attached together with no gasket or sealant.

Figure 13:
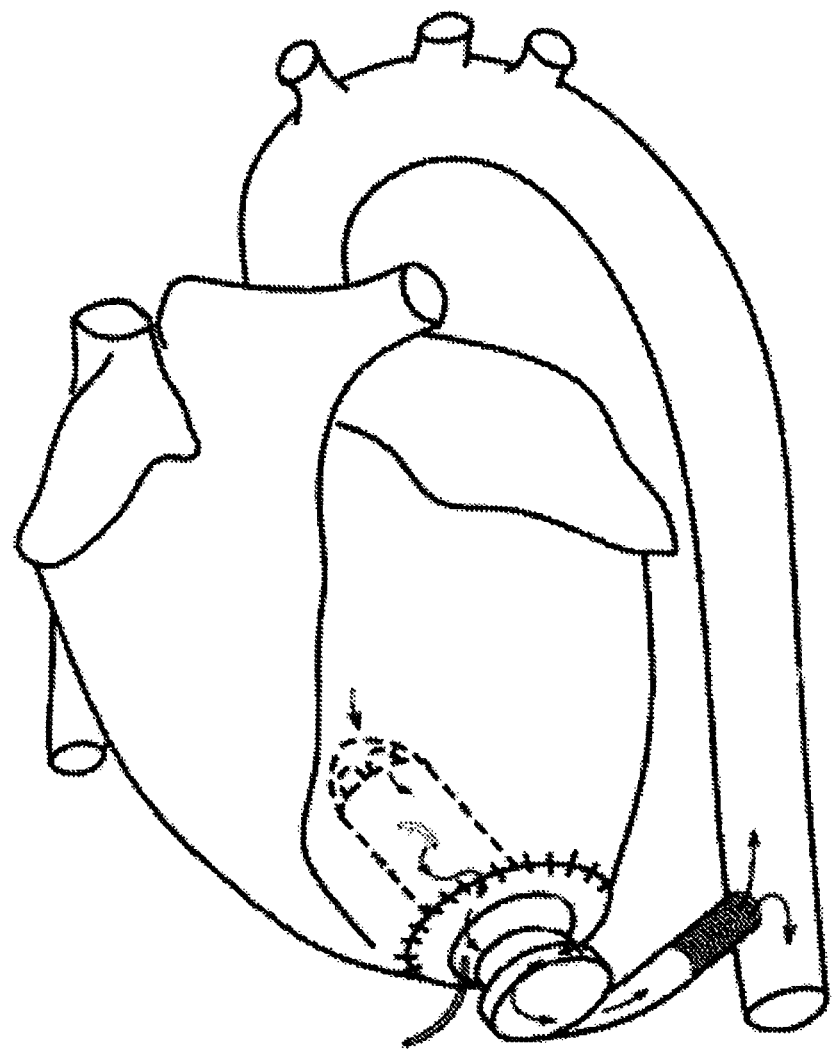
FIG. 13 illustrates a centrifugal casing and an outflow graft attached to the outflow tube are located outside the left ventricle, with the centrifugal casing near the apex, and the outflow graft connected to either the ascending aorta, or the descending aorta (prior art).

The pump of the preferred embodiment, as shown in the exploded view of FIG. 12, is adapted to be implanted with the motor portion and its housing placed within the left ventricle via the apex, in the same way the Jarvik 2000 heart is implanted. The centrifugal casing and an outflow graft attached to the outflow tube are located outside the left ventricle, with the centrifugal casing near the apex, and the outflow graft connected to either the ascending aorta, or the descending aorta. The position of the pump motor housing, volute, and graft is the same as in my previous U.S. Pat. No. 5,824,070. This is shown in FIG. 13.

The information disclosed in the description of the present invention is intended to be representative of the principles I have described. It will thus be seen that the objects of the invention set forth above and those made apparent from the preceding description are efficiently obtained and that certain changes may be made in the above articles and constructions without departing from the scope of the invention. It is intended that all matter contained in the above description and shown in the accompanying drawings shall be interpreted as illustrative but not in a limiting sense. It is also understood that the following claims are intended to cover all of the generic and specific features of the invention herein described and all statements of the scope of the invention which, as a matter of language, might be said to fall there between.

The invention claimed is:

1. A centrifugal or mixed flow blood pump comprising:
   two or three splitter blades, mounted within a pump casing that encloses an impeller, to form a triple volute or quadruple volute configured to distribute reverse blood flow throughout the pump casing and across substantially all surfaces of the impeller when the pump is unpowered,
   wherein the two or three splitter blades form three or four flow channels, respectively, and
   wherein the flow channels approximately equally distribute the reverse blood flow.

2. The blood pump of claim 1 in which a triple volute is formed by the casing and the impeller has three or six blades.

3. The blood pump of claim 1 in which a quadruple volute is formed by the casing and the impeller has four or eight blades.

4. The blood pump of claim 1 further comprising un-shrouded impeller blades configured to improve washing of the impeller when the pump is unpowered.

5. The blood pump of claim 1 in which the impeller is mounted on low friction blood immersed bearings.

6. A blood pump comprising:
   a centrifugal or mixed flow impeller mounted on a shaft supported by blood immersed bearings; and
   an axial flow impeller mounted to said shaft, wherein said axial impeller is configured to be driven by blood flowing in the reverse direction when the pump is unpowered.

7. The blood pump of claim 6 further comprising a triple or quadruple volute formed by a pump casing enclosing the impeller.

8. The blood pump of claim 6 in which the axial flow impeller is comprised of two or three generally helical axial pump blade portions, wherein a centrifugal type pump blade is joined downstream to each of said axial pump blade portions.

9. The pump of claim 8 further comprising centrifugal pump blades affixed to the impeller equi-distant from each of the centrifugal pump blades that are joined to the generally helical axial flow type blades.

10. A blood pump for use as a heart assist device comprising:
   a. A motor stator having an axial bore extending through it,
   b. A generally cylindrical motor rotor mounted on bearings within said axial bore, wherein an annular channel is formed between said motor stator and said motor rotor,
   c. The cross sectional area of said annular channel being small enough that its fluid flow resistance prevents a reverse blood flow in excess of about 0.75 L/min under physiological pressures when implanted in adults with heart failure in a position between the left ventricular apex and the aorta, and,
   d. a centrifugal pump impeller mounted to said generally cylindrical rotor for rotation within a casing having two or three splitter blades that divide the casing to form a triple or quadruple volute and distributes the reverse blood flow throughout the pump casing and across all surfaces of the impeller when the pump power is off.

11. A blood pump for use as a heart assist device comprising:
   a centrifugal or mixed flow impeller;
   a pump casing enclosing said impeller; and
   two to four splitter blades incorporated into the pump casing,
   wherein the splitter blades form three to five volute structures in the pump casing, respectively,
   wherein the three to five volute structures form three to five flow channels, and
   wherein said volute structures are configured to direct and approximately equally distribute a reversed blood flow across substantially all surfaces of the impeller.

12. The blood pump of claim 11 in which the impeller is configured to receive the directed reverse flow from the volute structures across substantially all surfaces of the impeller.

13. The blood pump of claim 11 further comprising:
   a rotor rigidly attached to said impeller; and
   a pump motor housing enclosing said rotor,
   wherein said rotor is supported within the housing by blood immersed bearings.

14. The blood pump of claim 11 further comprising:
   an axial flow impeller rigidly attached to said centrifugal or mixed flow impeller,
   wherein said axial flow impeller rotates in a reverse blood flow of less than 1 L/min through the pump.

* * * * *